(12) United States Patent
Daxer

(10) Patent No.: US 9,510,938 B2
(45) Date of Patent: Dec. 6, 2016

(54) CORNEAL IMPLANT AND METHOD FOR CORRECTION OF IMPAIRED VISION IN THE HUMAN EYE

(71) Applicant: Albert Daxer, Linz (AT)

(72) Inventor: Albert Daxer, Linz (AT)

( * ) Notice: Subject to any disclaimer, the term of this patent is extended or adjusted under 35 U.S.C. 154(b) by 150 days.

(21) Appl. No.: 13/653,609

(22) Filed: Oct. 17, 2012

(65) Prior Publication Data

US 2013/0041461 A1   Feb. 14, 2013

Related U.S. Application Data

(62) Division of application No. 12/227,533, filed as application No. PCT/EP2007/055015 on May 23, 2007, now abandoned.

(30) Foreign Application Priority Data

May 23, 2006   (AT) .................................. A 885/2006

(51) Int. Cl.
    *A61F 2/14*   (2006.01)
(52) U.S. Cl.
    CPC ................. *A61F 2/147* (2013.01); *A61F 2/14* (2013.01); *A61F 2/142* (2013.01); *A61F 2/1451* (2015.04)
(58) Field of Classification Search
    CPC ............ A61F 2/14; A61F 2/142; A61F 2/145; A61F 9/0017; A61F 2/147; A61F 2/1451
    USPC ................. 623/4.1–5.13, 5.16, 6.63
    See application file for complete search history.

(56) References Cited

U.S. PATENT DOCUMENTS

| 4,461,294 A | 7/1984 | Baron |
| 4,662,370 A | 5/1987 | Hoffmann et al. |
| 5,215,104 A | 6/1993 | Steinert |
| 5,342,378 A | 8/1994 | Giraud et al. |
| 5,549,632 A | 8/1996 | Lai |
| 5,556,406 A | 9/1996 | Gordon et al. |
| 5,624,456 A | 4/1997 | Hellenkamp |

(Continued)

FOREIGN PATENT DOCUMENTS

| DE | 34 33 581 | 3/1986 |
| EP | 0 712 297 | 5/1996 |

(Continued)

OTHER PUBLICATIONS

International Search Report in PCT/EP2007/055015 (corresponding PCT application), dated Sep. 13, 2007.
International Search Report in PCT/AT2007/000130, dated Aug. 8, 2007.
International Search Report in PCT/AT2004/000147, dated Aug. 31, 2004.
International Search Report of PCT/EP2010/052123, dated Jun. 11, 2010.

(Continued)

*Primary Examiner* — Howie Matthews
(74) *Attorney, Agent, or Firm* — Collard & Roe, P.C.

(57) ABSTRACT

Corneal implant to be introduced into the optical center (Z) of the cornea of the human eye for the purpose of correcting impaired vision, in particular presbyopia, or presbyopia in combination with hypermetropia or myopia. To propose a corneal implant which is suited for introduction into the optical center (Z) of the human eye, and which may be applied for correcting presbyopia on its own or in combination with hypermetropia or myopia, the effective thickness (d) of the corneal implant (2), measured in the direction of the optical axis (5) of the eye, must be larger than 50 μm and the maximum width (b), measured in a plane perpendicular to the direction of thickness, must be less than 1 mm, the corneal implant (2) having no imaging function in relation to the human eye.

6 Claims, 9 Drawing Sheets

(56) References Cited

U.S. PATENT DOCUMENTS

Figure 1:
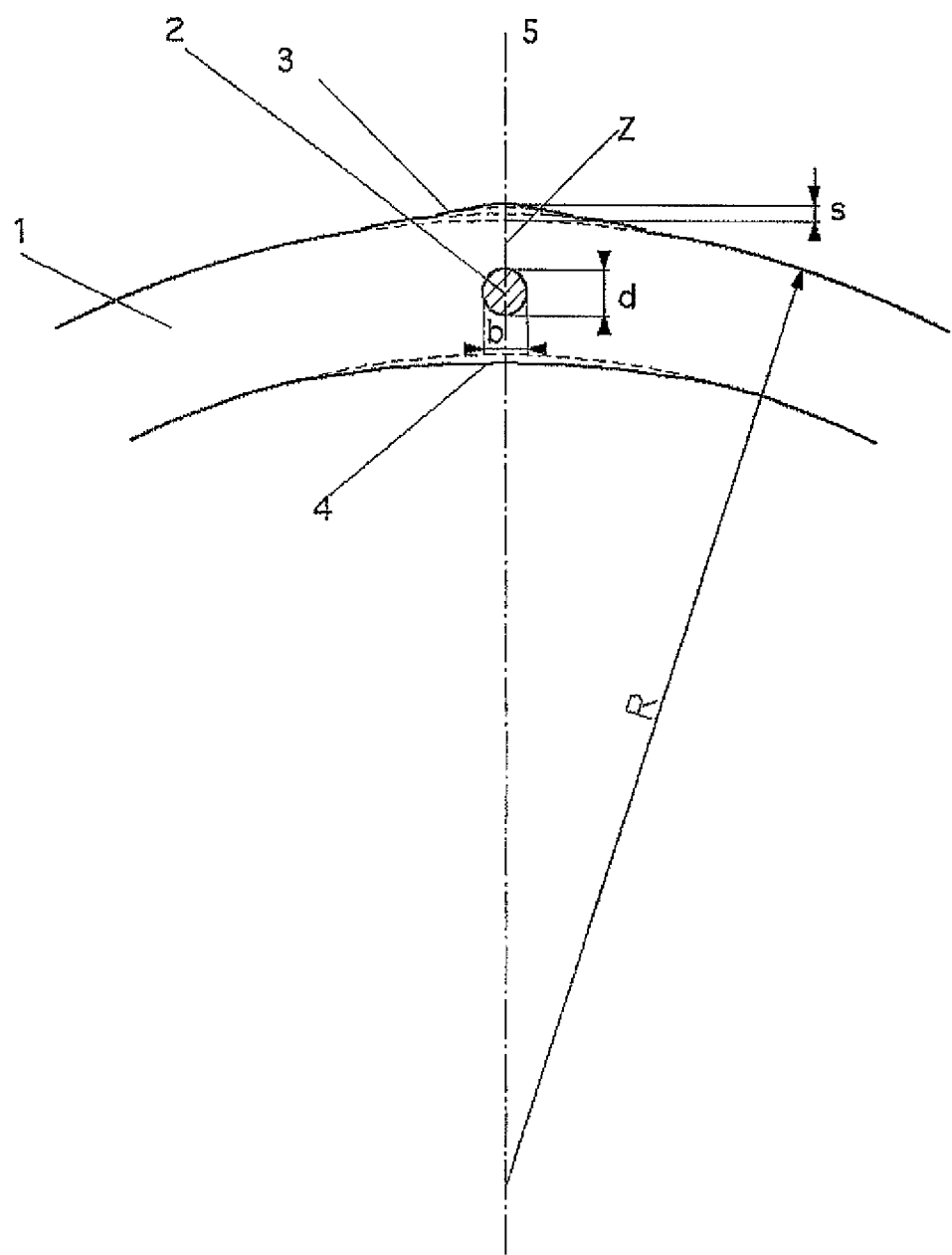

| | | |
|---|---|---|
| 5,634,943 A | 6/1997 | Villain et al. |
| 5,722,971 A | 3/1998 | Peyman |
| 5,817,115 A | 10/1998 | Nigam |
| 5,964,776 A | 10/1999 | Peyman |
| 6,056,764 A | 5/2000 | Smith |
| 6,083,236 A | 7/2000 | Feingold |
| 6,126,668 A | 10/2000 | Bair et al. |
| 6,132,446 A | 10/2000 | Hellenkamp et al. |
| 6,139,559 A | 10/2000 | Nordan et al. |
| 6,218,360 B1 | 4/2001 | Cintron et al. |
| 6,228,114 B1 | 5/2001 | Lee |
| 6,312,440 B1 | 11/2001 | Hood et al. |
| 6,358,262 B1 | 3/2002 | Chan et al. |
| 6,428,572 B2 | 8/2002 | Nagai |
| 6,506,198 B1 | 1/2003 | Amano |
| 6,543,453 B1 | 4/2003 | Klima et al. |
| 6,589,280 B1 | 7/2003 | Koziol |
| 6,599,305 B1 | 7/2003 | Feingold |
| 6,615,496 B1 | 9/2003 | Fleming et al. |
| 6,632,244 B1 | 10/2003 | Nigam |
| 6,679,605 B2 | 1/2004 | Zhou et al. |
| 6,923,821 B2 | 8/2005 | Wortrich |
| 8,071,135 B2 | 12/2011 | Liu et al. |
| 8,246,609 B2 | 8/2012 | Zickler et al. |
| 2001/0004702 A1 | 6/2001 | Peyman |
| 2001/0004708 A1 | 6/2001 | Nagai |
| 2001/0027314 A1 | 10/2001 | Peyman |
| 2002/0013622 A1 | 1/2002 | Hennig |
| 2002/0055753 A1 | 5/2002 | Silvestrini |
| 2002/0116056 A1* | 8/2002 | Kirk ............................. 623/5.11 |
| 2003/0033015 A1 | 2/2003 | Zhou et al. |
| 2004/0073303 A1 | 4/2004 | Schanzlin et al. |
| 2004/0143324 A1 | 7/2004 | Melles |
| 2004/0260320 A1 | 12/2004 | Lisk et al. |
| 2005/0080484 A1 | 4/2005 | Marmo et al. |
| 2005/0080485 A1 | 4/2005 | Nigam |
| 2005/0119738 A1 | 6/2005 | Nigam |
| 2005/0143717 A1 | 6/2005 | Peyman |
| 2005/0149006 A1 | 7/2005 | Peyman |
| 2006/0036318 A1 | 2/2006 | Foulkes |
| 2006/0116759 A1 | 6/2006 | Thornton et al. |
| 2006/0235513 A1 | 10/2006 | Price, Jr. |
| 2007/0016234 A1 | 1/2007 | Daxer |
| 2007/0142828 A1 | 6/2007 | Peyman |
| 2007/0203577 A1* | 8/2007 | Dishler .................. A61F 2/147 623/5.11 |
| 2008/0181967 A1 | 7/2008 | Liu et al. |
| 2009/0076601 A1 | 3/2009 | Daxer |
| 2009/0171305 A1 | 7/2009 | El Hage |
| 2009/0240327 A1 | 9/2009 | Daxer |
| 2010/0173019 A1 | 7/2010 | Paik et al. |
| 2010/0201944 A1 | 8/2010 | Lewis et al. |
| 2010/0256965 A1 | 10/2010 | Rathjen |
| 2011/0060267 A1 | 3/2011 | Dewoolfson et al. |
| 2012/0189583 A1 | 7/2012 | Liu et al. |

FOREIGN PATENT DOCUMENTS

| | | |
|---|---|---|
| EP | 1 229 856 | 8/2002 |
| EP | 1 364 633 | 11/2003 |
| EP | 1 620 049 | 2/2006 |
| GB | 2 095 119 | 9/1982 |
| RU | 2 256 430 | 7/2005 |
| WO | WO 93/05731 | 4/1993 |
| WO | WO 93/12735 | 7/1993 |
| WO | WO 93/14703 | 8/1993 |
| WO | WO 01/15779 | 3/2001 |
| WO | WO 01/49334 | 7/2001 |
| WO | WO 02/06883 | 1/2002 |
| WO | WO 03/015674 | 2/2003 |
| WO | WO 03/020176 | 3/2003 |
| WO | WO 03/020190 | 3/2003 |
| WO | WO 03/001965 | 11/2003 |
| WO | WO 2004/096106 | 11/2004 |
| WO | WO 2005/082265 | 9/2005 |

OTHER PUBLICATIONS

Russian Office Action dated Mar. 2, 2011 in Russian Patent Application No. 2008 145 675 (With German translation of same, along with an English translation of the German translation).

Eisner, "Eye Surgery: An Introduction to Operative Technique" Springer-Verlag Berlin Heidelberg 1978, pp. 67-69.

Daxer A. et al., "Collagen Fibrils in the Human Corneal Stroma: Structure and Aging," Invest. Opthalmol & Vis. Sci, Mar. 1998, vol. 39, No. 3, pp. 644-648.

Spoerl E, Huhle M, Seiler T., "Induction of cross-links in corneal tissue", Abstract Exp. Eye Res., Jan. 1998; 66(1):97-103; 1 page.

Spörl, E.; Huhle, M.; Kasper, M. and Seiler, T., "Erhöhung der Festigkeit der Hornhaut durch Vernetzung", Ophthalmologe, vol. 94, No. 12 (Dec. 1997), pp. 902-906 (with English Abstract).

Schnitzler, E.; Spörl, E. and Seiler, T., "Bestrahlung der Hornhaut mit UV-Licht und Riboflavingabe als neuer Behandlungsversuch bei einschmelzenden Hornhautprozessen, erste Ergebnisse bei vier Patienten", Klin Monatsbl Augenheilkd, vol. 217, No. 3 (Sep. 2000) pp. 190-193 (with English Abstract).

Ronald R. Krueger, MD, MSE; Jerome C. Ramos-Esteban, MD; A. John Kanellopoulos, MD. Staged Intrastromal Delivery of Riboflavin With UVA Cross-linking in Advanced Bullous Keratopathy: Laboratory Investigation and First Clinical Case. Journal of Refractive Surgery, vol. 24, pp. S730-S736, Sep. 2008.

Albert Daxer, MD, PhD. Intracorneal ring: A good alternative to Lasik? Ophthalmology Times Europe, vol. 3, Issue 8. Oct. 1, 2007.

Ocular Surgery News Europe Edition. Corneal cross-linking shows increasingly good results, gains popularity, stimulates research. Ocular Surgery News, vol. 20, No. 8. Sep. 2009.

Stanley A. Klein and Robert B. Mandell, "Shape and Refractive Powers in Corneal Topography," Investigative Ophthalmology & Visual Science, Sep. 1995, vol. 36, No. 10, pp. 2096-2109.

Peter Fratzl and Albert Daxer, "Structural transformation of collagen fibrils in corneal stroma during drying," Biophys. J., Biophysical Society, vol. 64, Apr. 1993, pp. 1210-1214.

Albert Daxer and Peter Fratzl, "Collagen Fibril Orientation in the Human Corneal Stroma and Its Implication in Keratoconus," Investigative Ophthalmology & Visual Science, Jan. 1997, vol. 38, No. 1, Association for Research in Vision and Ophthalmology, pp. 121-129.

Albert Daxer; Klaus Misof; Barbara Grabner; Armin Ettl and Peter Fratzl, "Collagen Fibrils in the Human Corneal Stroma: Structure and Aging," IOVS, Reports, Mar. 1998, vol. 39, No. 3, pp. 644-648.

Albert Daxer, MD, PhD., "Adjustable Intracorneal Ring in a Lamellar Pocket for Keratoconus," Journal of Refractive Surgery, vol. 26, No. 3, 2010, pp. 217-221.

Albert Daxer, MD, PhD., "Corneal intrastromal implantation surgery for the treatment of moderate and high myopia," J Cataract Refract Surg 2008; 34, ASCRS and ESCRS, pp. 194-198.

Douglas R. Wilson, M.D. and Arthur H. Keeney, M.D., D.Sc., "Corrective Measures for Myopia," Diagnostic and Surgical Techniques, Steven G. Kramer, Editor, Survey of Ophthalmology, vol. 34, No. 4, Jan.-Feb. 1990, pp. 294-304.

Austin W. Chang et al., "Corneal tissue ablation depth and the Munnerlyn formula," J Cataract Refract Surg 2003; 29, ASCRS and ESCRS, pp. 1204-1210.

Mulet et al., Hydrogel Intracorneal Inlays for the Correction of Hyperopia—Outcomes and Complications after 5 Years of Follow-up, Ophthalmology, vol. 116, No. 8, Aug. 2009, pp. 1455-1460.e1.

Ferrer et al., Causes of intrastromal corneal ring segment explantation: Clinicopathologic correlation analysis, J Cataract Refract Surg—vol. 36, Jun. 2010, pp. 970-977.

\* cited by examiner

Fug. 5g 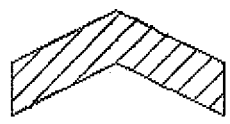

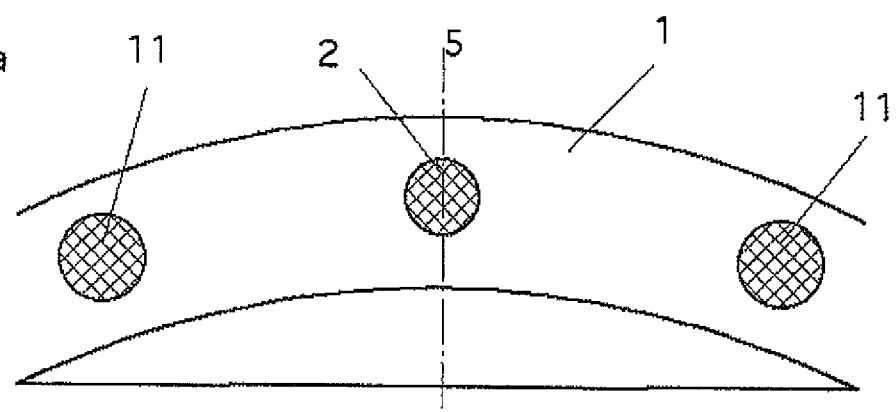
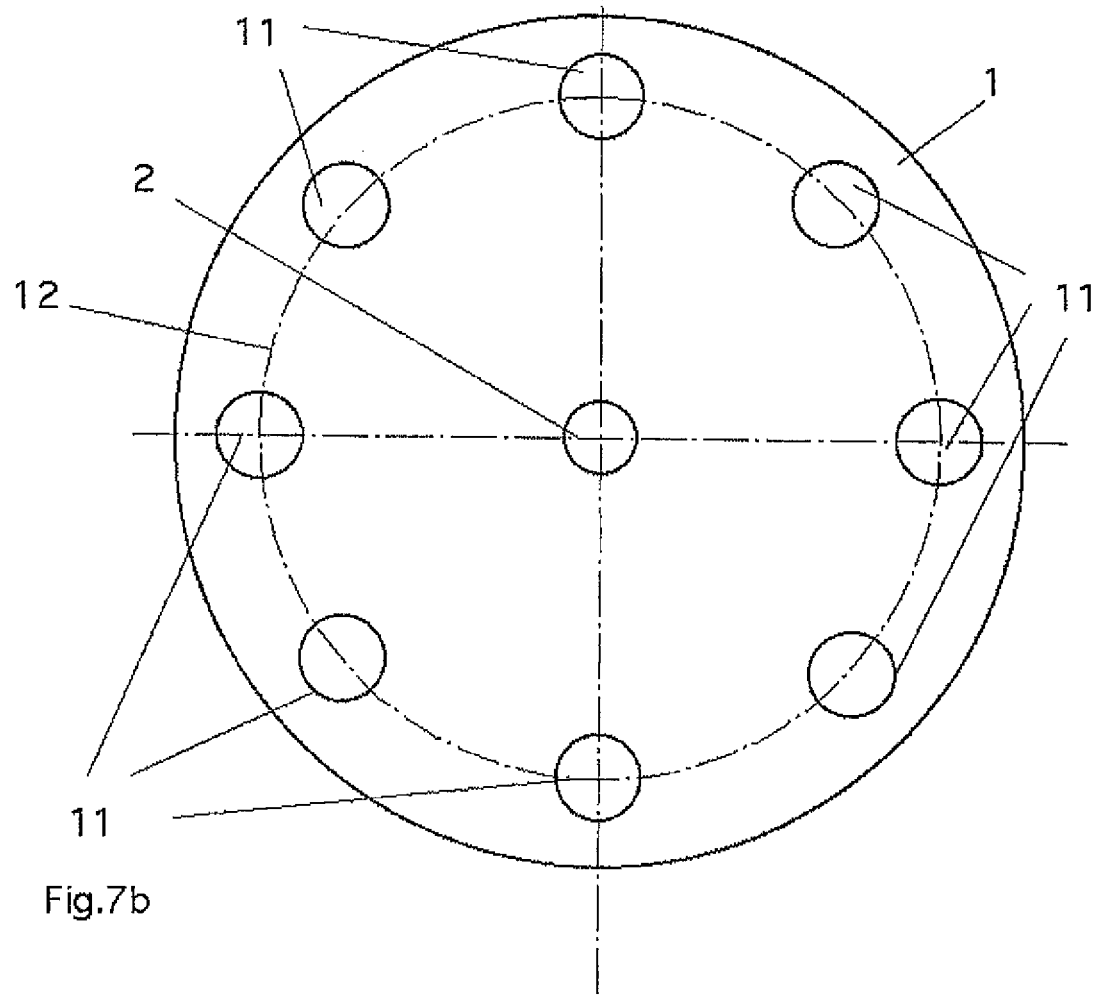

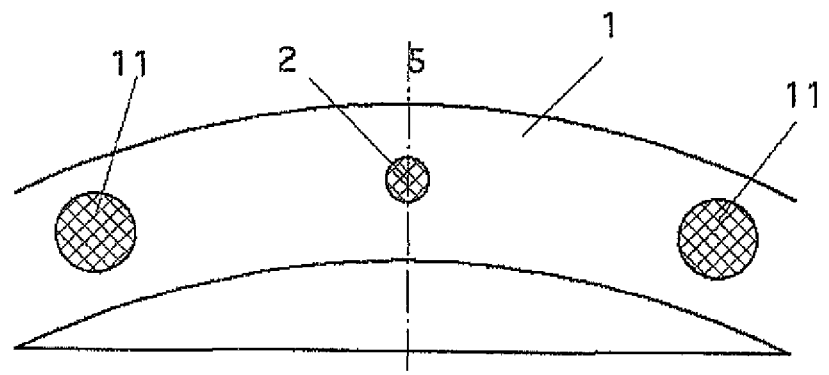
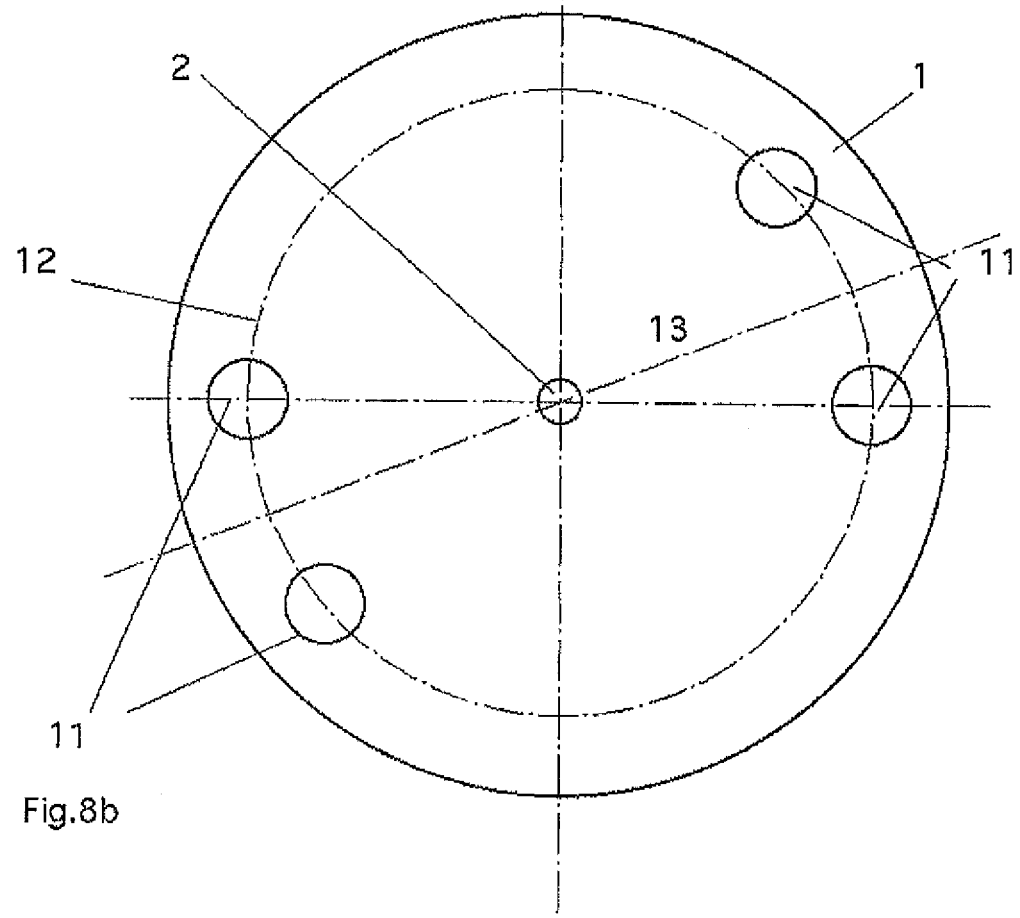

CORNEAL IMPLANT AND METHOD FOR CORRECTION OF IMPAIRED VISION IN THE HUMAN EYE

CROSS REFERENCE TO RELATED APPLICATIONS

This application is a divisional of and Applicant claims priority under 35 U.S.C. §§120 and 121 of parent U.S. patent application Ser. No. 12/227,533 filed Nov. 20, 2008, which application is a national stage application under 35 U.S.C. §371 of PCT/EP2007/055015 filed on Mar. 23, 2007, which claims priority under 35 U.S.C. §119 of Austrian Application No. A 885/2006 filed May 23, 2006, the disclosures of each of which are hereby incorporated by reference. The international application under PCT article 21(2) was not published in English.

AREA OF THE INVENTION

The present invention relates to a corneal implant to be inserted into the optical center of the cornea of the human eye for the purpose of correcting impaired vision, in particular presbyopia in otherwise emmetropic eyes (eyes with normal vision) as well as presbyopia in combination with hypermetropia (farsightedness) or myopia (nearsightedness).

The present invention furthermore relates to a procedure for correcting impaired vision in the human eye, in particular for correcting presbyopia, presbyopia in combination with hypermetropia, presbyopia in combination with myopia, and presbyopia in combination with astigmatism, by inserting a corneal implant into the optical centre of the cornea.

The optical apparatus of the human eye that generates an optical image of the environment basically comprises the cornea and the lens, which is positioned behind the iris. This optical apparatus of the eye has a total refractive power of approximately 60 dioptres, with the interface between the cornea and the air—i.e. the outer boundary of the eye—with approximately 40 dioptres accounting for most of the refractive power. This refractive power of the cornea is in general indirectly proportionate to the radius of the corneal surface (interface between cornea and air). A change in the radius of the curvature of the cornea also leads to a change in the refractive power of the eye.

In the case of myopia or nearsightedness, the eyeball is too long and the refractive power of the cornea thus inadequate to assure that the light rays are focussed on the retina; these are focussed in front of the retina instead.

In the case of hypermetropia or farsightedness, the eyeball is too short and the refractive power of the cornea thus insufficient to assure that the light rays are correctly focussed on the retina; they are focussed behind the retina instead.

Presbyopia is a dissociation of the refractive power of the eye in that for accurate far vision a different correction of dioptres than for accurate near vision is required.

Different options for correcting these refractive errors are available. In addition to the classical methods of vision correction via glasses or contact lenses, also surgical methods are known where implants are inserted into the cornea of the human eye with the aim to either modify the curvature of the cornea and thus correct the refractive power of the latter accordingly, or to alter the optical properties of the cornea through the optical properties of the implant.

By enlarging the radius of curvature of the cornea the refractive power is reduced, which allows to correct a myopic condition. To be able to correct a hyperopic condition, the corneal radius needs to be reduced, i.e. the curvature needs to be increased.

To be able to correct presbyopia by surgical intervention, it is necessary to impart a certain degree of bi-focality or multi-focality to the refractive power of the cornea. This means that the refractive power of the cornea is designed in a way that the light rays entering the eye from different distances (near or far away), depending on their point of entry, are simultaneously focussed on the retina, or more precisely in the central area of the retina (=the macula, the area where accurate vision occurs). This implies that one or several images from a far distance and one or several images from a near distance are simultaneously focussed in the macula. The brain then selects the appropriate image. To allow this selection to take place, the far-away image and the near image must have about the same intensity. The use of contact lenses and intraocular lenses, which are inserted after cataract surgery, are based on this principle.

STATE OF THE ART

WO 93/05731 reports the insertion of an optical lens into the optical center of the cornea, the dimensions of which are smaller than those of the optical zone being limited by the diameter of the pupil.

The optical center of the cornea is that part of the cornea along which the optical axis of the eye passes through the cornea. The optical axis is the axis of projection of the optical system of the eye. The ophthalmologist determines the optical center by using specific assessment methods. The ophthalmologist may choose from a wide variety of different methods. The methods for determining the optical center of the cornea described hereinafter represent only a small portion of the many different methods commonly applied, and are not exhaustive. Many systems, in particular excimer laser systems with active eye tracking, use the center of the pupil or its projection on the corneal surface or around a point at an individually defined distance as the optical center of the cornea. Other common systems are aimed at the area where the curvature of the cornea is most pronounced. Especially in the case of high-degree myopia, in fact, an angular deflection of the optical axis from the anatomical axis is to be noticed, which is defined as the "kappa angle". Another method relates to the so-called "Purkinje reflexes". These are reflexes on the corneal front and back faces as well as on the lens front and back faces, which occur when the patient focuses on a preferably point-shaped light source. While these reflexes ideally overlap, most of the time this is not the case; the eye specialist then chooses one of these reflexes as the optical center. It is also quite common to choose the middle position of all four reflexes, or the middle between this middle position and the center of the pupil etc. Eventually, it is left to the personal discretion, individual experience and preference of the eye specialist how he determines the optical center of the cornea. Generally speaking, the various methods used for determining the optical center of the cornea tend to render quite similar results.

In WO 93/05731, the implantation of an optical lens in the optical center of the cornea results in various zones of different refractive power, namely in the area of the optical lens itself as well as in the adjoining corneal tissue through the refractive power of the cornea proper. This allows to create a certain degree of bifocality or multifocality, depending on the contour of the optical surface of the implanted lens. The thickness of the lenses in the direction of the optical axis of the eye is less than 50 µm to avoid an undesirable deflection of the cornea and an impairment of the refractive power of the lens. Basically, however, there is the disadvantage that the newly created boundary surfaces may produce optically adverse phenomena such as glares and reflections, which the patient will find disturbing. The optical surface therefore needs to be excellently designed, which in case of such small dimensions is a rather difficult and tedious undertaking. It is also known that organic deposits tend to form along the boundaries of corneal implants, which may substantially impair the function of the implants as optical elements.

U.S. Pat. No. 6,589,280 B1 describes a method of creating a multi-focal cornea by implanting a minimum of 50 microscopically small optical lenses outside the optical center of the cornea. Each lens should have a defined refractive power, preferrably 1 to 3 dioptres. The optical lenses have a thickness of approx. 2-3 µm and a width of less than 1 mm (measured in a plane perpendicular to the direction of thickness). The lenses are so small that the curvature of the cornea is not impaired by the deflection of the corneal surface. The refractive error is corrected exclusively through the different refractive power of the individual lenses. The described method is extremely complicated and, with regard to its usability in living tissue, the same arguments as mentioned earlier apply.

U.S. Pat. No. 5,722,971 describes a method where a thin plate-shaped implant with diffractive optics and a hole at its center is implanted. The outer diameter is in a range between 3 mm and 9 mm. In addition, ring implants as well as ring replacement implants are presented. In this case, the ring is replaced by several individual implants which are concentrically positioned along a circle around the center of the cornea. By leaving individual positions of the circle empty, not only myopic conditions but also regular and irregular astigmatisms may be corrected. No reference is made to the dimensions of the replacement implants, but the illustrations provided reveal that in order for the replacement implants to have the same effect as the rings, they must replace about the same volume and therefore, as is also shown in the drawings, must have a much bigger size and dimensions that correspond to the pupil width or iris width. Moreover, there is no detailed information as to their geometry. The illustrated applications imply that they must have the shape of a protracted ellipsoid. Such implants are not suited for use in the area of the central cornea.

The same applies with respect to US 2004/0073303 A1, where the preferred embodiment of the invention is even a curved, protracted implant (centroid).

A state-of-the-art method therefore is to implant optical lenses as corneal implants in the optical center of the cornea. These optical corneal implants exert their effect via their own refractive power. They have an optically effective front and/or back face and also contain a material with a specific refractive index, which is positioned between the optically effective front and/or back face and defines both the contour and the refractive power of these optical corneal implants. It is also known, however, that in such optical corneal implants there is the tendency that in the area of contact with the surrounding tissue purely optical phenomena occur and organic material is deposited. Especially in implants which are inserted into the optical center of the human eye, this leads to a significant impairment of vision.

Although implants positioned outside of the optical center are less sensitive to the aforementioned deposits, they are not able to create bi-focality let alone multi-focality to correct presbyopia on its own or in combination with hypermetropia or myopia.

DESCRIPTION OF THE INVENTION

The aim of the present invention therefore is to suggest a corneal implant which is suited for introduction into the optical center of the human eye and which may be used to correct presbyopia on its own as well as presbyopia in combination with hypermetropia (farsightedness) or myopia (nearsightedness).

According to the invention, this is achieved through the characteristics described herein. The aim is to provide the corneal implant with an effective thickness, measured in the direction of the optical axis of the eye, of more than 50 µm and a maximum width, measured in a plane perpendicular to the direction of thickness, of less than 1 mm, the corneal implant having no imaging function in relation to the human eye.

A corneal implant of the selected dimensions is on one hand suited for being positioned in the optical center of the human eye without impairing the vision of the human eye, and on the other also suited for correcting presbyopic vision by modifying the curvature of the cornea through corneal deflection in its optical center. Since a corneal implant according to the invention has no imaging function in relation to the human eye, which means that it has no optical effect whatsoever, it is relatively easy to produce. The dimensions according to the invention allow to introduce the implant directly into the optical center of the eye without reducing its vision. Resulting from the central addition of volume an aspherical surface contour of the cornea may be produced in the surroundings of the corneal implant, which facilitates a multi-focal image so as to correct presbyopic vision. Corrections of hyperopic conditions are possible as well. The implantation in the optical center of the cornea implies that the implant, with due consideration of the finite defining accuracy of the optical center and the finite positioning accuracy of the implant in the cornea, is introduced into the cornea along a line that represents the optical center, i.e. the line along which the optical axis passes through the cornea.

Contrary to the state of the art, the implant deliberately fails to support optical imaging. The optical effect of the implant is thus indirectly achieved and determined by the contour of the transitional area in the adjoining tissue. Since the implant according to the invention has no direct optical imaging function, it needs no optically designed surfaces. The implant surfaces may be flexibly shaped and are not bound by optical requirements such as in optically effective implants. The geometry of the implant is exclusively determined by geometrical considerations regarding the type of replacement of the tissue surrounding the implant. What was said also implies that an implant according to the invention which corresponds to a preferred embodiment of the invention need not be transparent, but may also be opaque or partly transparent and of any sort of color in order to assume its function according to the invention. Since under certain conditions (geometry) disturbing surface phenomena may occur at the transparent faces (similar to optical implants), while the geometry may display a favourable tissue replacement behaviour, this side effect may be eliminated by eliminating or reducing the transparency of the corneal implant. In case a colour is to be added to the corneal implant, black has proven to be particulary advantageous as it does not stand out from the underlying black color of the pupil.

In any case, in an implant according to the invention, even if it were made of transparent material, the proportion of light rays entering the implant after its introduction into the cornea in no way contributes to the perception of a retinal image, which means it fails to project a perceivable image on the retina. Among other things, this stems from the dimensions and measurements of the implants according to the invention, their geometry, their surface properties, their material, their color, optical losses occurring along the area of contact with the surrounding tissue as well as biological interaction with the surrounding tissue. This is particularly the case if the implant has been embedded in the tissue for a certain period of time. This, in particular, makes the effect of the implant insensitive to optical and biological surface phenomena, by which it differs from state-of-the-art products.

Since the eye complies with the laws of geometrical optics, and the latter basically corresponds to the optics of the rays close to the axis, an expert would expect that by introducing a non-optical body—typically representing an optical obstacle—into the optical center of the cornea, the vision would be substantially impaired. Surprisingly, it could be shown that if this body has the characteristics according to the invention, such impairment will only be minimal.

In a preferred embodiment of the invention, the ratio between width and effective thickness of an implant according to the invention is less than three and/or more than one. It has been shown that in this case particularly positive results regarding multi-focality can be achieved.

Effective thicknesses of less than 500 μm and width variations not exceeding 30 percent of the largest width also help to adjust the outline of the corneal surface to the requirements of multi-focal imaging.

In another preferred embodiment of the invention, the corneal implant is rotation-symmetrically arranged around the axis along the effective thickness. In a particularly preferred embodiment, the corneal implants have the shape of a sphere, thus assuring an ideal formation of the aspherical surface contour on the corneal surface.

It is yet a further task of the present invention to suggest a method for the correction of impaired vision in the human eye, in particular for the correction of presbyopia on its own or in combination with hypermetropia, by inserting a corneal implant into the optical center of the human eye without risking that the function of the implant is impaired by deposits in the optical center of the cornea around the implant and without the need to use sophisticated optical lenses as implants.

According to the invention, this task is achieved through the characteristics of methods described herein of implanting one or several corneal implants into the optical center of the cornea to deflect the surface of the cornea.

The aim is to introduce into the optical center of the cornea of the human eye one or several corneal implants without an imaging function in relation to the human eye, each of which has an effective thickness of more than 50 μm, measured in the direction of the optical axis of the eye, and a maximum width of less than 1 mm, measured in a plane perpendicular to the direction of thickness, with the purpose of modifying the curvature of the corneal surface around the optical center of the cornea through deflection of the corneal surface in the optical center.

Another task of the present invention is to suggest a method for the correction of impaired vision in the human eye, in particular for the correction of presbyopia in combination with myopia, by introducing a corneal implant into the optical center of the human eye without risking that the function of the implant is impaired by deposits in the optical center of the cornea around the implant and without the need to use sophisticated optical lenses as implants.

According to the invention, this task is achieved through the characteristics described here. The aim is to introduce into the optical center of the cornea one or several corneal implants without an imaging function in relation to the human eye, which have an effective thickness of more than 50 μm, measured in the direction of the optical axis of the eye, and a maximum width of less than 1 mm, measured in a plane perpendicular to the direction of thickness, for the purpose of accomplishing a deflection of the surface of the cornea in its optical center; several corneal implants, preferably one ring-shaped corneal implant, are additionally positioned outside the optical center of the cornea, assuring that the curvature of the cornea outside the optical center is modified.

The following is a detailed description of the invention using examples of embodiments, from which the expert may deduce additional advantages of the invention. The figures show the following:

SHORT DESCRIPTION OF THE DRAWINGS

Figure 2:
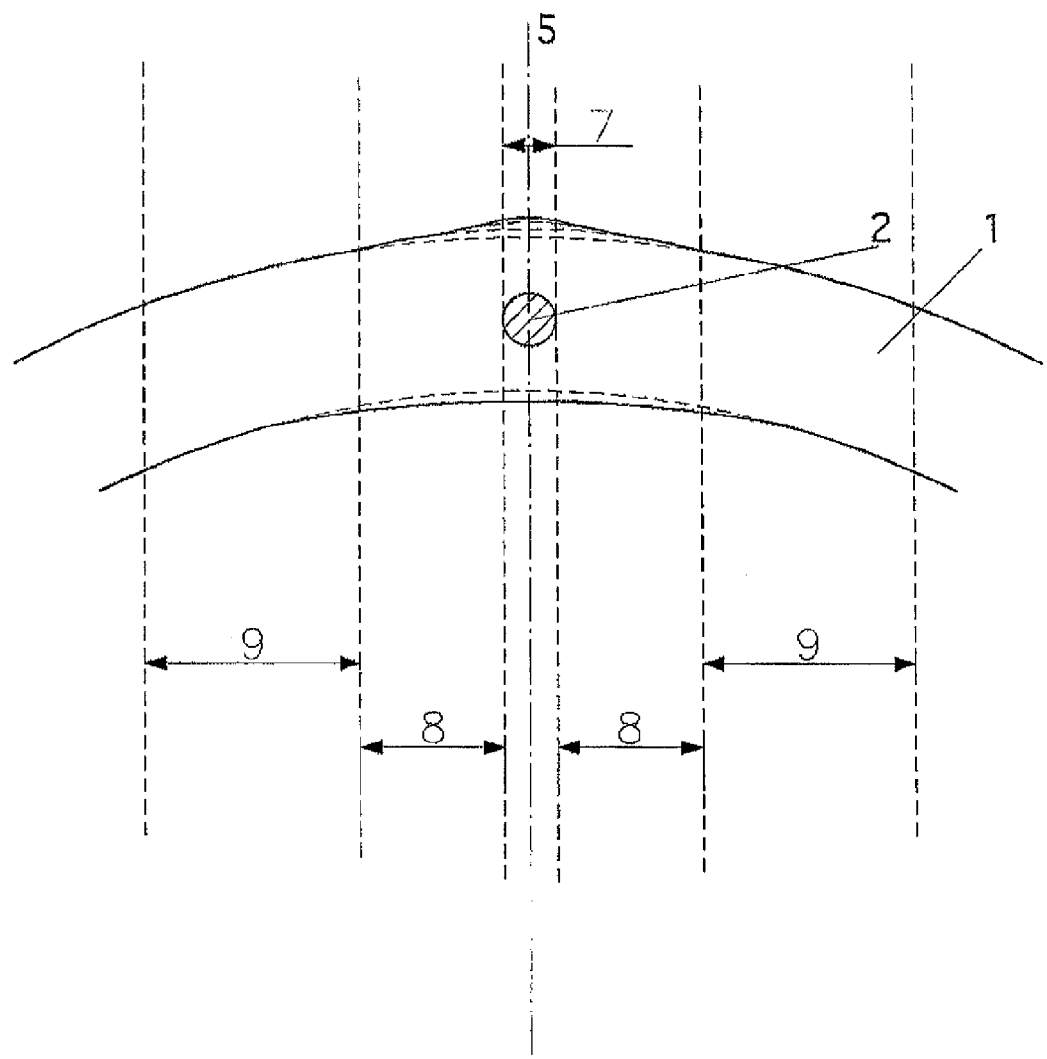
Figure 3:
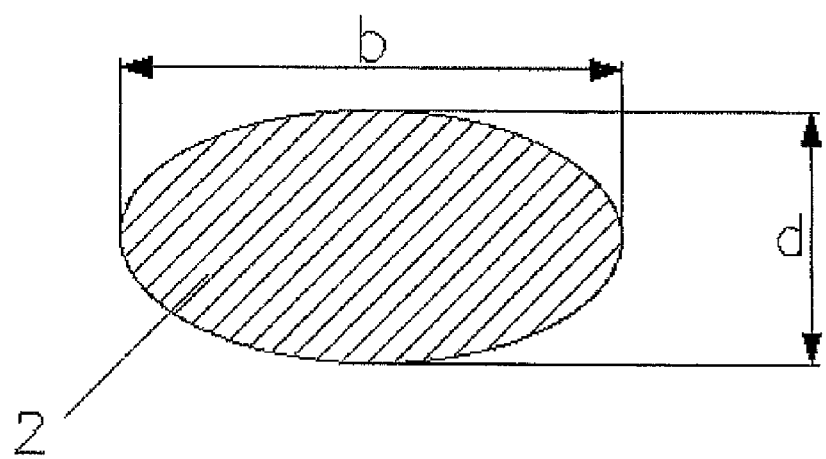
Figure 4:
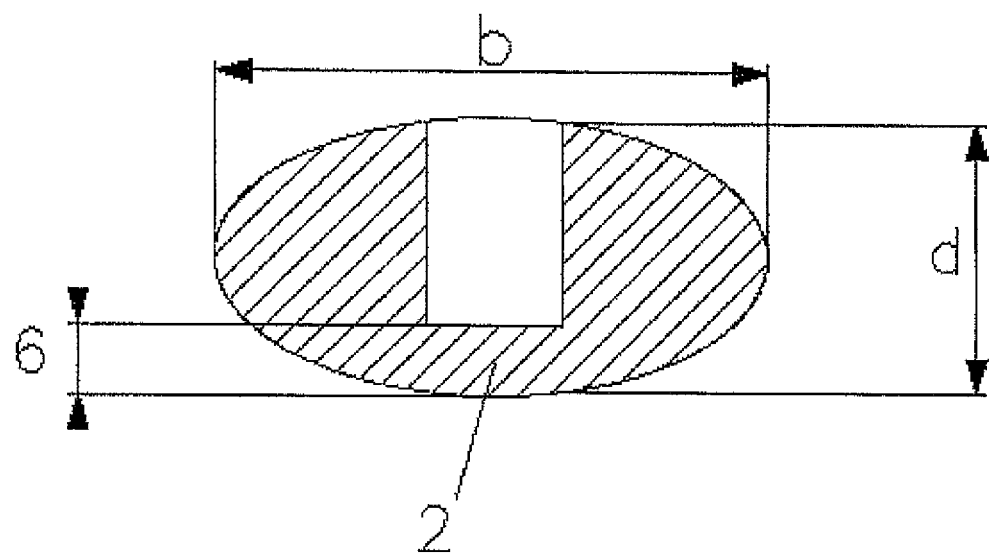
Figure 5A:
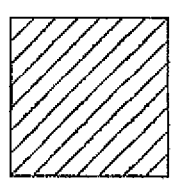
Figure 5B:
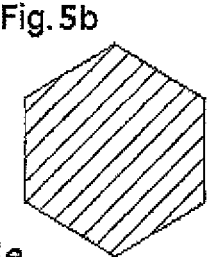
Figure 5C:
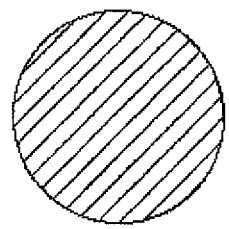
Figure 5D:
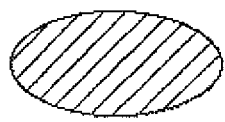
Figure 5E:
Figure 5F:
Figure 5H:
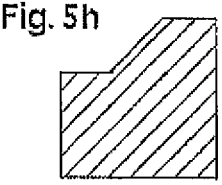
Figure 5I:
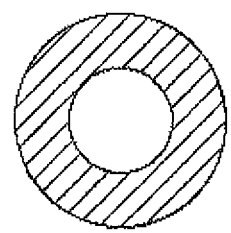
Figure 5J:
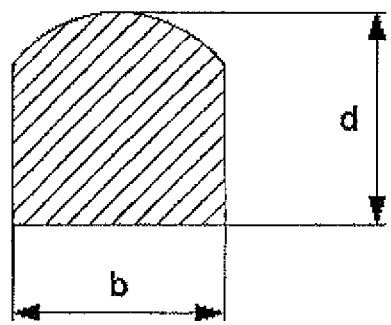
Figure 5K:
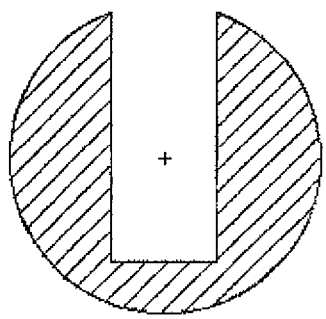
Figure 5L:
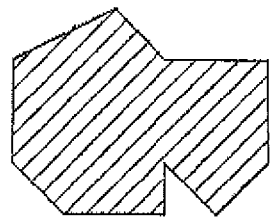
Figure 5M:
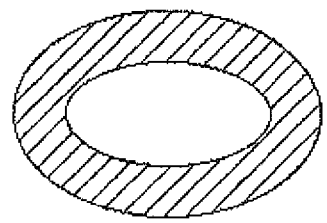
Figure 5N:
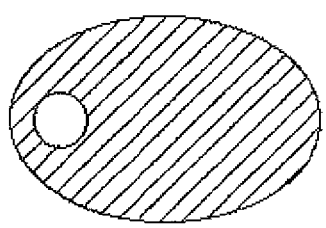
Figure 5O:
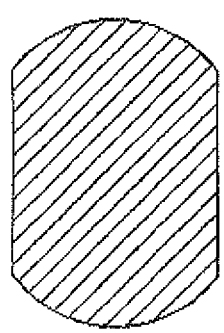
Figure 5P:
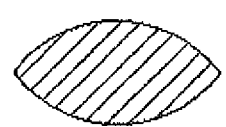
Figure 5Q:
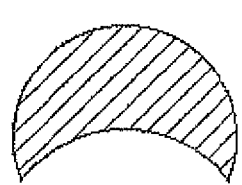
Figure 5R:
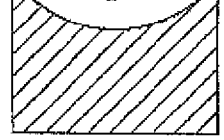
Figure 5S:
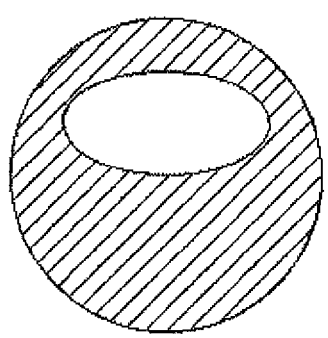
Figure 6A:
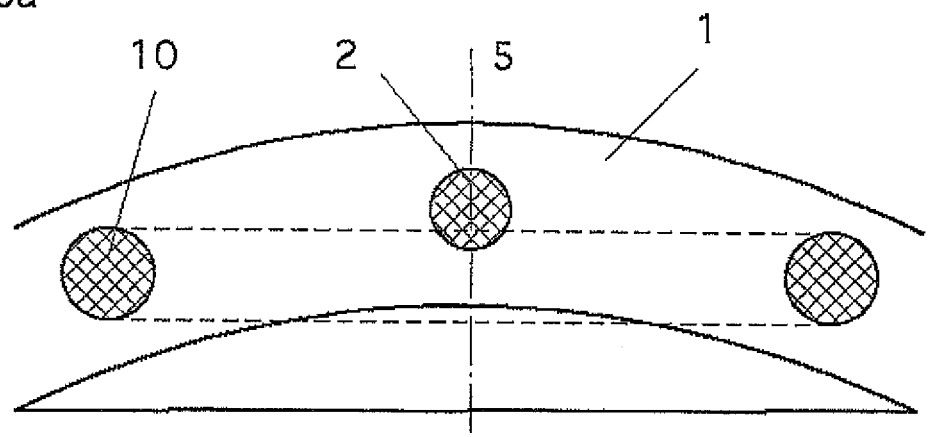
Figure 6B:
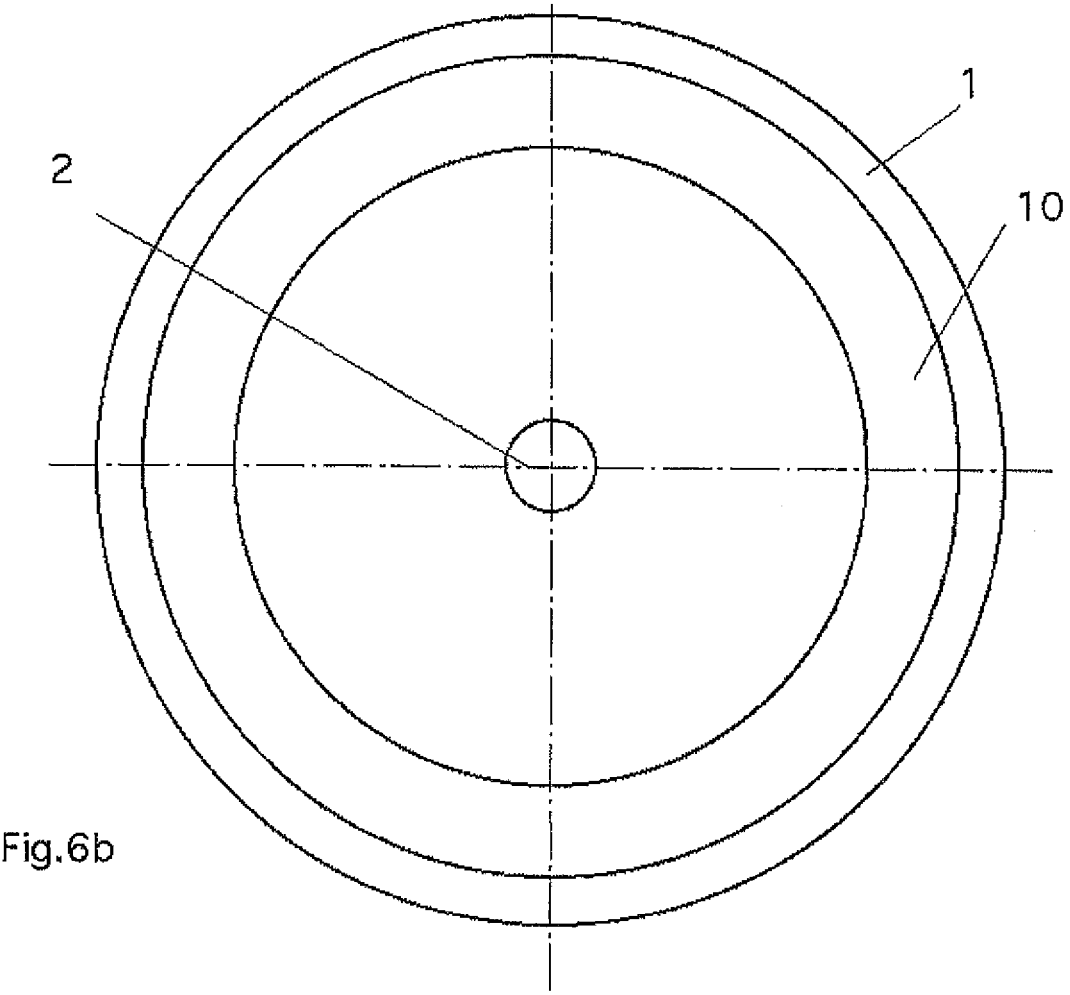

FIG. 1 cross section of the cornea of a human eye with an implanted corneal implant in keeping with the invention FIG. 2 cross section of the cornea of a human eye with an implanted corneal implant in keeping with the invention, where the different effective areas are marked FIG. 3 cross section of a corneal implant in keeping with the invention FIG. 4 cross section of an alternative corneal implant in keeping with the invention FIG. 5a-s further alternative cross sections of corneal implants according to the invention FIG. 6a-b corneal implant according to the invention in combination with a ring-shaped corneal implant FIG. 7a-b corneal implant according to the invention in combination with several individual corneal implants FIG. 8a-b corneal implant according to the invention in combination with several individual aligned corneal implants

WAYS TO EXECUTE THE INVENTION

FIG. 1 shows a cross section of the cornea 1 of a human eye with a radius of curvature R including an optical center Z. A corneal implant 2 according to the invention is implanted in the corneal tissue of the cornea 1, having an effective thickness d of more than 50 μm, measured in the direction of the optical axis 5 of the eye, and a width b of less than 1 mm, measured in a plane perpendicular to the direction of thickness.

The corneal implant 2 has no imaging function in relation to the human eye, which means that the light rays entering the eye are not focussed on the retina (not depicted in the drawings) of the eye due to the optical properties of the corneal implant 2 according to the invention. Instead, the implantation of the corneal implant 2 results in a central volume addition and thus in an aspherical surface contour 3 of the cornea 1 around the optical center Z of the cornea, which also facilitates multi-focal imaging.

In contrast to the known state-of-the-art corneal implants and vision correction methods, the aim of the present invention is to introduce a corneal implant 2 into the optical center Z of the eye which deliberately lacks an optical function and which serves to correct the impaired vision exclusively by altering the curvature R of the cornea 1 around the corneal implant.

While this also leads to deformations in the area of the corneal back face 4, these are of only minor relevance for vision correction.

In keeping with the invention, the corneal implant 2 may be of any type of transparency: it may be fully opaque, semi-transparent, or fully transparent. Based on the fact that the corneal implant 2 has no imaging function in relation to the eye, it may be of any color whatsoever, preferrably black to assure compatibility with the black pupil.

FIG. 2 shows a cross section through the cornea 2 of a human eye in which a corneal implant 2 according to the invention is inserted, including markings of the different effective areas of the cornea 1. The central corneal area 7, which is defined by the size of the implant 2, is not directly involved in the visual process. The peripherally adjoining area 8 shows the aspherical surface contour with the resulting property of multi-focal imaging. Then comes the corneal area 9 that remains unaffected by the corneal implant 2.

Depending on the dimensions of the corneal implant 2, there is the possibility to add refractive power for near vision to the area 8, whereas area 9 is intended for far vision. The latter is peripherally confined by the pupil diameter.

The embodiment according to FIGS. 1 and 2 presents the use of a corneal implant 2 which is rotation-symmetrically arranged around the axis of the effective thickness, thus having the shape of a sphere and being limited to 1 mm diameter in size. As far as the aspherical surface contour 3 of the cornea 2 and the multi-focal imaging properties are concerned, such a sphere-shaped corneal implant 2 produces exceptionally positive results.

To the expert it is clear, however, that a corneal implant 2 according to the invention may basically have any shape and yet be capable of solving the task underlying the invention, provided the implant has a minimum effective thickness of 50 µm, measured in the direction of the optical axis 5 of the eye, and a maximum width of 1 mm, measured in a plane perpendicular to the direction of thickness.

It is important to note that due to the introduction of a corneal implant 2 into the optical center of the cornea 1, the curvature R of the cornea around the optical center changes significantly.

The ratio between the width and the effective thickness of the corneal implant should ideally not exceed factor 3 and/or fall below factor 1 to assure acceptable multi-focal imaging properties for the patient. Another requirement is that the width alongside the circumference must not vary by more than 30 percent of the largest width.

FIG. 3 shows a cross section through a corneal implant 2 according to the invention, which has an elliptic cross section with an effective thickness d and a width b.

FIG. 4 shows a cross section of an alternative corneal implant 2 according to the invention, with which the same effect in keeping with the invention may be achieved as with the corneal implant 2 depicted in FIG. 3, as long as a minimum effective thickness of 50 µm and a maximum width of 1 mm as indicated above are observed. The expert immediately notices that while cavities, such as those schematically represented in FIG. 4, reduce the thickness of the corneal implant 2 to a minimum thickness 6 in some sections, the effective thickness d remains unaffected therefrom and thus the effect to be achieved according to the invention is not impacted. Consequently, a corneal implant 2 as depicted in FIG. 4 allows to change the curvature R of the cornea 1 in the optical center of the cornea 1, while at the same time leaving the vision unimpaired.

FIG. 5a to 5s show further potential cross sections of corneal implants 2 according to the invention which, provided that they fulfill the requirements regarding a minimum effective thickness and a maximum permissible width, support the aspherical surface contour 3 of the cornea 1 required for multi-focal vision.

The invention is based on the assumption that a deflection of the cornea 1 is required in order to achieve the desired effect, i.e. the outside measurements of the corneal implant 2 as well as its elasticity need to be adjusted to the elasticity of the cornea 1 and the compression inside the tissue in such a way that the desired deflection and the related aspherical surface contour 3 is achieved. This can be accomplished by using a corneal implant with an effective thickness of more than 50 µm; by limiting the width to below 1 mm, a relevant vision impairment and a nutrition deficiency of the cornea can be prevented and the implantation into the optical center can be achieved.

The material used for the implant may be any type of biocompatible material such as PMMA, HEMA, acryl-containing materials, plastics, metals, semi-conductors, insulators, or other materials commonly used in this field of application.

The method for producing an implant bed does not differ from the known techniques. The implant bed may, for example, be produced by using a LASIK keratome, by cutting a largely enclosed corneal pocket, as described in EP 1 620 049 B1, or by creating a narrow corneal tunnel.

The corneal implant 2 according to the invention primarily serves to correct a presbyopic condition, but also presbyopia in combination with hypermetropia. It may also be introduced in combination with other known corneal implants, for instance in combination with ring implants as shown in FIG. 6, by which presbyopia in combination with myopia can be corrected.

FIG. 6a-b show a known ring-shaped corneal implant 10 which is implanted outside the optical center of the cornea 1, as well as a corneal implant 2 according to the invention which is implanted in the optical center of the cornea 1, producing the aspherical surface contour 3. Instead of a ring-shaped corneal implant 10, also individual small implants 11, as shown in FIG. 7a-b, may be applied outside the optical center of the cornea 1.

The corneal implants 2 and 10 or 11 together serve to correct presbyopia in combination with myopia due to the change of curvature of the corneal surface, even though the implants have no optical effect.

In FIG. 7, the small implants 11 are arranged along a circular line 12 around the optical center. If the small implants 11 have different sizes, in addition to presbyopia and myopia also astimgatism may be corrected.

If the corneal implants 2 and 11 are arranged as illustrated in FIG. 8 so that a preferred axis 13 is created, also astigmatic vision may be corrected.

Due to the complex curvature of the corneal surfaces in FIGS. 6,7 and 8, the surface is only schematically represented, without the curvature being changed by the corneal implants 2, 10 and 11.

It needs to be noted in particular that elements of embodiments according to the invention may be combined with elements of other embodiments according to the invention, and that these combinations again represent embodiments according to the invention.

What is claimed is:

1. Method for the correction of refractive errors in the human eye, in particular for the correction of presbyopia on its own or in combination with hypermetropia, by introducing a corneal implant (2) into an optical center (Z) of the cornea (1) of the human eye, including the following step:

Introducing a corneal implant (2) into the cornea into an optical center (z) of the cornea, the optical center being defined by a line along which an optical axis passes through the cornea, said implant having an effective thickness (d) of more than 50 µm and less than 500 µm measured in a direction of the optical axis as well as width (b) of less than 1 mm measured in a plane perpendicular to the direction of thickness, where said implant is rotation-symmetrically arranged around the optical axis along the effective thickness, wherein said introducing said implant into the cornea deforms an area of a corneal back face and modifies a curvature (R) of a corneal surface through a corneal deflection into an aspherical surface contour around the optical center as determined by a specific type of replacement of tissue from adding a volume of the implant to the cornea and generating different effective areas of the cornea including a central corneal area (7) defined by the width (b) of the implant and not directly involved in a visual process of the eye while said implant is an optical obstacle, and while said implant has no imaging function in relation to the eye, an adjoining area (8) showing the aspherical surface contour (3) from the at least one corneal deflection with a resulting added refractive power and multi-focal imaging function for near vision, and an area (9) peripherally confined by a pupil diameter and which for far vision remains unaffected by the corneal implant, and wherein the corneal implant is opaque and, therefore, not transparent to visible light.

2. Method according to claim 1, wherein the ratio between the width (b) and the effective thickness (d) is less than three.

3. Method according to claim 1, wherein the corneal implant (2) has the shape of a sphere.

4. Method according to claim 1, wherein the corneal implant (2) is black.

5. Method according to claim 1, wherein the implant has an elliptic cross section with the effective thickness d and the width b.

6. Method according to claim 1, wherein the the ratio between the width (b) and the effective thickness (d) is higher than one and less than twenty.

* * * * *